United States Patent
Lee

(10) Patent No.: US 10,682,225 B2
(45) Date of Patent: Jun. 16, 2020

(54) FLEXIBLE INTRAOCULAR LENS HAVING MULTIPLE YOUNG'S MODULI

(71) Applicant: ALCON INC., Fribourg (CH)

(72) Inventor: Sung Kyu Lee, Euless, TX (US)

(73) Assignee: Alcon Inc., Fribourg (CH)

( * ) Notice: Subject to any disclaimer, the term of this patent is extended or adjusted under 35 U.S.C. 154(b) by 45 days.

(21) Appl. No.: 15/897,235

(22) Filed: Feb. 15, 2018

(65) Prior Publication Data

US 2018/0235751 A1 Aug. 23, 2018

Related U.S. Application Data

(60) Provisional application No. 62/462,648, filed on Feb. 23, 2017.

(51) Int. Cl.
*A61F 2/16* (2006.01)
*B33Y 80/00* (2015.01)

(52) U.S. Cl.
CPC ........ *A61F 2/16* (2013.01); *A61F 2002/1681* (2013.01); *A61F 2002/1686* (2013.01); *A61F 2002/16905* (2015.04); *A61F 2250/0018* (2013.01); *B33Y 80/00* (2014.12)

(58) Field of Classification Search
CPC .............. A61F 2/16; A61F 2002/16905; A61F 2002/1681; A61F 2002/1686
See application file for complete search history.

(56) References Cited

U.S. PATENT DOCUMENTS

| | | | |
|---|---|---|---|
| 7,840,455 B1 | 11/2010 | Venkatasubramanian et al. | |
| 2006/0161252 A1 | 7/2006 | Brady et al. | |
| 2008/0249820 A1 | 10/2008 | Pathria et al. | |
| 2011/0246262 A1 | 10/2011 | Pepper et al. | |
| 2012/0143327 A1 | 6/2012 | Bumbalough | |
| 2013/0297018 A1* | 11/2013 | Brady ............... | A61F 2/1618 623/6.37 |
| 2015/0182330 A1* | 7/2015 | Grant ............... | A61F 2/1624 623/6.37 |
| 2016/0358268 A1 | 12/2016 | Verma et al. | |

OTHER PUBLICATIONS

Patent Cooperation Treaty, International Search Report and Written Opinion, International Application No. PCT/IB2019/000807, dated Dec. 2, 2019, 12 pages.

* cited by examiner

*Primary Examiner* — David H Willse
*Assistant Examiner* — Tiffany P Shipmon

(57) ABSTRACT

A method and system provide an ophthalmic device including an optic and a haptic. The optic includes at least one optical material having a first Young's modulus. The haptic is coupled with the optic. The haptic includes at least a second Young's modulus greater than the first Young's modulus and less than 1.8 GPa. Thus, the haptic is stiffer than the optic, but more flexible than a material such as polymethyl metacrylate (PMMA).

9 Claims, 5 Drawing Sheets

FLEXIBLE INTRAOCULAR LENS HAVING MULTIPLE YOUNG'S MODULI

FIELD

The present disclosure relates generally to ophthalmic lenses and more particularly to a flexible intraocular lens having multiple Young's moduli.

BACKGROUND

Intraocular lenses (IOLs) are implanted in patients' eyes either to replace a patient's lens or to complement the patient's lens. An IOL typically includes an optic and haptics. The optic, or lens, corrects the patient's vision typically via refraction or diffraction. Haptics are support structures used to hold the optic in place within the capsular bag of a patient's eye. In some cases, haptics take the form of arms that are coupled to the optic. In some IOLs, the haptics and optic are formed of the same flexible optical material. In order to possess sufficient mechanical strength to hold the optic in place, the haptics for such lenses are frequently significantly thicker than the optic. Stated differently, the volume of the haptics may be relatively high in such IOLs. Alternatively, other IOLs form the haptics from a stiff material such as polymethyl metacrylate (PMMA). The stiff haptics are typically of constant cross-section and attached at a point to the softer optic.

In general, a physician selects an IOL having the appropriate corrective characteristics for the patient. During ophthalmic surgery, often performed for other conditions such as cataracts, the selected IOL is implanted. To do so, the surgeon makes an incision in the capsular bag of the patient's eye. The IOL is inserted through the incision and set in place. The incision is closed after the IOL is in place.

Although the IOLs function acceptably well in most patients, implanting the IOL may have shortcomings. A relatively large incision may be required for IOL implantation. Large incisions are considered to be more invasive and may adversely affect the patient's recovery. For an IOL having PMMA haptics, an incision may be greater than or equal to 2.4 mm in length. Such a large incision is required to accommodate the stiff haptics. In addition, larger incisions may cause surgically induced astigmatism. This is also an undesirable outcome. Further, the transition between the haptic arms and optic may be unstable because of the significant differences in the characteristics of the materials. Thus, the IOL may also be subject to failure during implantation or once in place. For an IOL formed only of a single material, the higher volume haptics as well as the optic may still require a larger incision than is desired.

Accordingly, what is needed is an improved mechanism for implanting an IOL.

BRIEF SUMMARY OF THE INVENTION

A method and system provide an ophthalmic device including an optic and a haptic. The optic includes at least one optical material having a first Young's modulus. The haptic is coupled with the optic. The haptic includes at least a second Young's modulus greater than the first Young's modulus and less than 1.8 GPa. Thus, the haptic is stiffer than the optic, but more flexible than a material such as PMMA.

According to the method and system disclosed herein, the haptic may be made thinner but still support the softer material used in the optic. The haptic and optic may also be deformable. Thus, a physician may be better and more easily able to implant the ophthalmic device through a smaller incision. Further, the materials used for the haptic and their Young's moduli may be tailored to improve the performance of the haptic. Consequently, performance of the ophthalmic device may be improved.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE PREFERRED EMBODIMENTS

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein. The method and system are also described in terms of singular items rather than plural items. One of ordinary skill in the art will recognize that these singular terms encompass plural. For example, a chamber may include one or more chambers.

A method and system provide an ophthalmic device including an optic and a haptic. The optic includes at least one optical material having a first Young's modulus. The haptic is coupled with the optic. The haptic includes at least a second Young's modulus greater than the first Young's modulus and less than 1.8 GPa. Thus, the haptic is stiffer than the optic, but more flexible than a material such as PMMA. The haptics may include multiple Young's moduli. Higher Young's moduli material(s) may be used for locations on the haptics that correspond to higher stresses. Thus, the haptics may be formed of multiple materials.

Figure 1A:
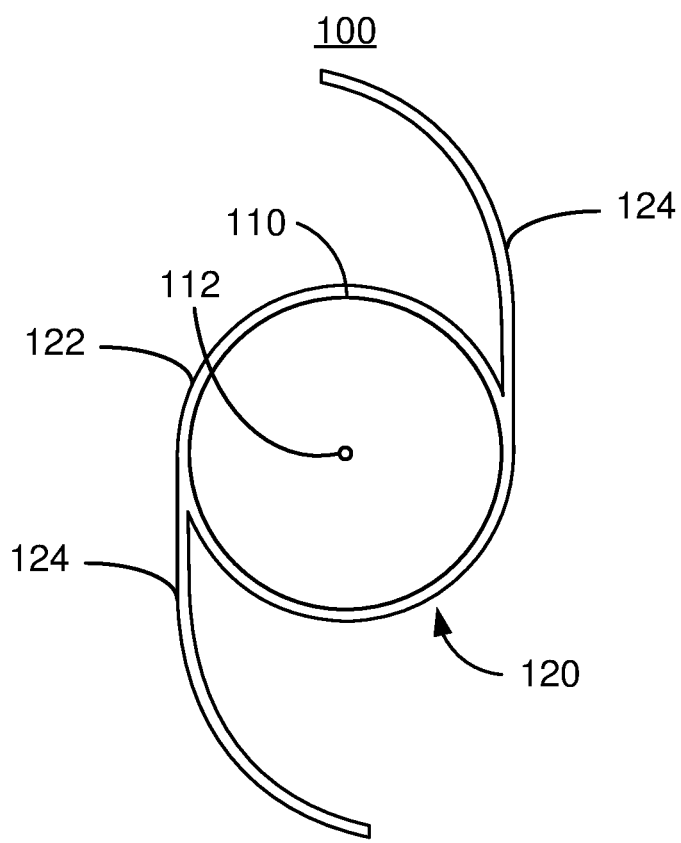
FIGS. 1A and 1B depict various views of an exemplary embodiment of an ophthalmic lens having multiple Young's moduli.
Figure 1B:
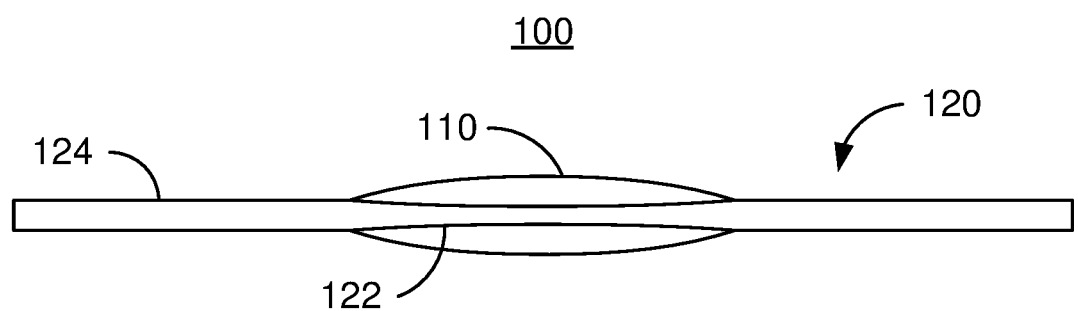

FIGS. 1A and 1B depict an exemplary embodiment of an ophthalmic device 100 having multiple Young's moduli and that may be used as an IOL. For simplicity, the ophthalmic device 100 is also referred to as an IOL 100. FIG. 1A depicts a plan view of the IOL 100, while FIG. 1B depicts a side view of the ophthalmic device 100. For clarity, FIGS. 1A-1B are not to scale. The IOL 100 includes an optic 110 as well as a haptic 120. The optic 110 is an ophthalmic lens 110 that may be used to correct a patient's vision. The haptic 120 is a support structure used to hold the ophthalmic device 100 in place in the capsular bag of a patient's eye (not explicitly shown).

The optic 110 has an optic axis 112. Although the optic 110 is depicted as having a circular cross section in the plan view of FIG. 1A, in other embodiments, other shapes may be used. The anterior and/or posterior surface of the optic 110 may have features including but not limited to a base curvature and diffraction grating(s). The optic 110 may thus refract and/or diffract light to correct the patient's vision. In some embodiments, the optic 110 may also include other features that are not shown for clarity. The optic 110 may be fabricated using one or more of a variety of flexible optical materials. For example, the optic 110 may include but is not limited to one or more of silicone, a hydrogel and an acrylic such as AcrySof®. The optic 110 may be relatively soft and flexible. Thus, the optic 110 may be formed of material(s) that may bend for implantation in the capsular bag.

The haptic 120 includes a frame 122 and arms 124. Although particular shapes are shown for the frame 122 and arms 124, one of ordinary skill in the art will recognize that the shape of the frame 122 and arms 124 may differ in other embodiments. For example, the arms 124 may be configured as plates or loops. Similarly, shape the frame 122 may differ. The inner portion of the frame 122 may be desired to match the shape of the optic 110. Thus, the inner edge of the frame 122 is shown as circular in FIG. 1A. In other embodiments, the optic 11 and inner edge of the frame 122 may have another shape. The outer edge of the frame 122 can but need not match the inner edge.

The frame 122 couples the haptic 120 with the optic 110. In some embodiments, the frame 122 may be bonded to the optic 110. In other embodiments, the frame 122 may be otherwise attached to the optic 110. For example, the frame 122 may be molded into the optic 110. The arms 124 retain the IOL 100 in position in the patient's eye.

The haptic 120 includes one or more materials having a higher Young's modulus than the optic 110. In some embodiments, all portions of the haptic 120 have a higher Young's modulus than any portion of the optic 110. Thus, the haptic 120 is stiffer than the optic 110. The haptic 120 also has a Young's modulus that is less than 1.8 GPa. Thus, the Young's modulus of the haptic 120 is less than that of stiff materials such as PMMA. Consequently, the haptic 120 is flexible (though less so than the optic 110). The haptic 120 is, however, still capable of holding the IOL 100 within the capsular bag of the patient's eye and maintaining the desired shape of the optic 110. Materials that might be used for the haptics 120 include but are not limited to combination(s) of biocompatible IOL materials such as Silicone, urethane, acrylic and/or other analogous materials. These materials have been used for building IOLs. However the ratio(s) of the basic chemical components of such materials may be adjusted to achieve the desired target Young's modulus for both the optic 110 and haptics 120. Thus, such materials may be used for both components 110 and 120, but the stoichiometry of the materials tailored such that the haptic 120 has a higher Young's modulus than the optic 110 and such that the haptic 120 remains flexible (has a lower Young's modulus than PMMA).

In the embodiment shown in FIGS. 1A and 1B, the haptic 120 is formed of a single material having a Young's modulus that is higher than that of the optic 110 and lower than that of PMMA. In other embodiments, the haptic 120 is formed of multiple materials having different Young's moduli. The Young's modulus of locations in the haptic 120 may be tailored to provide various advantages. In addition, the haptic 120 is depicted as having different cross sectional areas for the arms 124 than for the frame 122. As can be seen in FIG. 1B, therefore, the frame 122 is thinner than the arms 124. In other embodiments, the frame 122 and arms 124 may have the same cross-sectional area. In other embodiments, frame 122 may have a higher cross-sectional area than the arms 124. The cross-section of the haptic 120 may differ at different portions of the haptic 120. Thus, the combination of the cross-sectional area and the Young's modulus of portions of the haptic 120 may be tailored to provide the desired stiffness and size.

In addition to supporting and retaining the optic 110 in place, the haptic 120 may also be configured for other purposes. For example, the haptic 120 may have one or more sharp edges (not shown in FIGS. 1A-1B). Such edges may address posterior capsular opacification (PCO) by preventing or reducing the growth and/or migration of cells. Such a sharp edge is made possible through the use of higher Young's modulus material(s) in the haptic 120.

Use of the IOL 100 may improve patient outcomes. Because higher Young's modulus material(s) are used for the haptic 120 than for the optic 110, the volume of the haptic 120 may be reduced. Because the Young's modulus material(s) of the haptic 120 are sufficiently low to still be flexible, the IOL 100 may be deformed during implantation. As a result, a smaller incision may be used for implantation. This less invasive surgery may reduce complications and improve the patient's recovery. Because the frame 122 may be used to retain the optic 110, softer (lower Young's modulus) material(s) may be used for the optic 110 than might be used in other conventional IOLs. Thus, the optic 110 may allow for a larger deformation during implantation. The optic volume may also be reduced. This reduction in volume and stiffness may also reduce the size of the incision used. In some embodiments, multiple materials may be used for the haptic 120. As a result, the stiffness of various sections of the haptic 120 may be tailored for various purposes. Thus, the performance of the haptic 120 both during implantation and throughout its lifetime may be improved. Use of the higher Young's modulus material(s)

may also allow sections of the haptic 120 to be shaped for other purposes. Thus, performance of the IOL 100 may be further improved.

Figure 2:
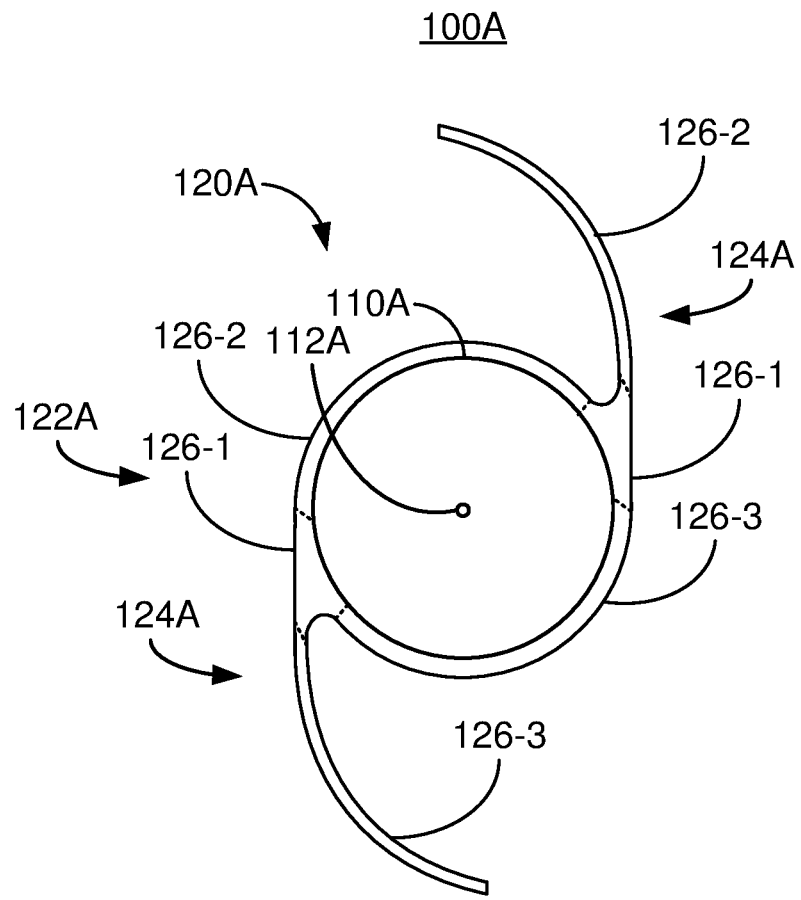
FIG. 2 depicts another exemplary embodiment of an ophthalmic device having multiple Young's moduli.

FIG. 2 depicts a plan view of another exemplary embodiment of an ophthalmic device 100A having multiple Young's moduli and that may be used as or in an IOL. For simplicity, the ophthalmic device 100A is also referred to as an IOL 100A. For clarity, FIG. 2 is not to scale. The IOL 100A is analogous to the IOL 100. Consequently, analogous components have similar labels. The IOL 100A thus includes haptic 120A and optic 110A that are analogous to the haptic 120 and optic 110, respectively. The haptic 110A includes frame 122A and arms 124A that are analogous to the frame 122 and arms 124, respectively. The optic 110A has an optic axis 112A. Although not shown, the anterior and/or posterior surface of the optic 110A may have other features including but not limited to a base curvature and diffraction grating(s). The optic 110A may be fabricated using one or more of a variety of optical materials, as discussed above. The optic 110A may be relatively soft and flexible.

The haptic 120A includes a frame 122A and arms 124A. Although particular shapes are shown for the frame 122A and arms 124A, one of ordinary skill in the art will recognize that the shape of the frame 122A and arms 124A may differ in other embodiments. The frame 122A couples the haptic 120A with the optic 110A. The arms 124A retain the IOL 100A in position in the patient's eye.

The haptic 120A explicitly includes multiple materials having different Young's moduli. Thus, the haptic 120A is shown as having regions 126-1, 126-2 and 126-3 having three different Young's moduli. Because these regions 126-1, 126-2 and 126-3 are all part of the haptic 120A, the regions 126-1, 126-2 and 126-3 are shown as separated by dotted lines. Although three regions 126-1, 126-2 and 126-3 having certain shapes are shown, another number of regions that may have different shapes may be present in other embodiments. In some embodiments, all regions 126-1, 126-2 and 126-3 of the haptic 120A have a higher Young's modulus than any portion of the optic 110. In some embodiments, each portion 126-1, 126-2 and 126-3 also has a Young's modulus that is less than 1.8 GPa. In alternate embodiments, only some of the regions 126-1, 126-2 and 126-3 have a Young's modulus in this range.

The haptic 120A is formed of multiple materials having different Young's moduli in locations that may be selected to provide various advantages. For example, locations that are expected to experience higher stresses may have a higher Young's modulus. Such regions may include the area in which the arms 124A meet the frame 122A. Thus the regions 126-1 may have a higher Young's modulus than the regions 126-2 and 126-3. The Young's modulus of portions in the haptic 120A may be tailored for other reasons. For example, the tips of the arms 124A that bear against the capsular bag may have a different Young's modulus than other portions of the arms 124A and/or frame 122A. Similarly, the inner portion(s) of the frame 122A that are affixed to the optic 110 may have a lower Young's modulus than the outer edges of the frame 122A. Alternatively, regions 126-2 of the arms 124A may be made higher Young's modulus material than the regions 126-3 of the frame. In some embodiments, the cross-section of the haptic 120A may differ at different portions of the haptic. Thus, the combination of the cross-sectional area and the Young's modulus of portions of the haptic 120A may be tailored to provide the desired stiffness and size.

In the embodiment shown in FIG. 2, the number, size, shape, Young's modulus and other characteristics of the regions 126-1, 126-2 and 126-3 may be determined in various ways. For example, the stresses, strains and other conditions to which the IOL 100A may be subject during implantation and use may be modeled. The desired characteristics of the regions such as regions 126-1, 126-2 and 126-3 may be determined through this modeling, for example using structural finite element analysis. The desired materials having the desired stiffness for each portion of the haptic 120A may thus be ascertained. Portions of the haptic 120A may then be bonded together or otherwise fabricated. For example, the haptic 120A may be machined, injection molded, casted, printed using a three-dimensional (3-D) printer, or formed in another manner. Use of a 3-D printer may allow for a monolithic structure to be formed from different material(s) and/or having different Young's moduli.

The IOL 100A may share the benefits of the IOL 100. Because higher Young's modulus materials are used for the haptic 120A than for the optic 110A, the volume of the haptic 120A may be reduced. Because the Young's modulus materials of the haptic 120A are sufficiently low, the haptic 120A is still flexible. Thus, the IOL 100A may be deformed during implantation. As a result, a smaller incision may be used for implantation. This less invasive surgery may reduce complications and improve the patient's recovery. Because the frame 122A may be used to retain the optic 110A, softer material(s) that allow for larger deformations may be used for the optic 110A. The optic volume may also be reduced. This reduction in volume and stiffness of the optic may also reduce the size of the incision used. In addition, the use of multiple materials for the haptic 120A allows for the stiffness of various sections of the haptic 120A may be tailored to withstand higher stresses or strains. Thus, the performance of the haptic 120A both during implantation and throughout its lifetime may be improved. Consequently, performance of the IOL 100A may be further improved.

Figure 3:
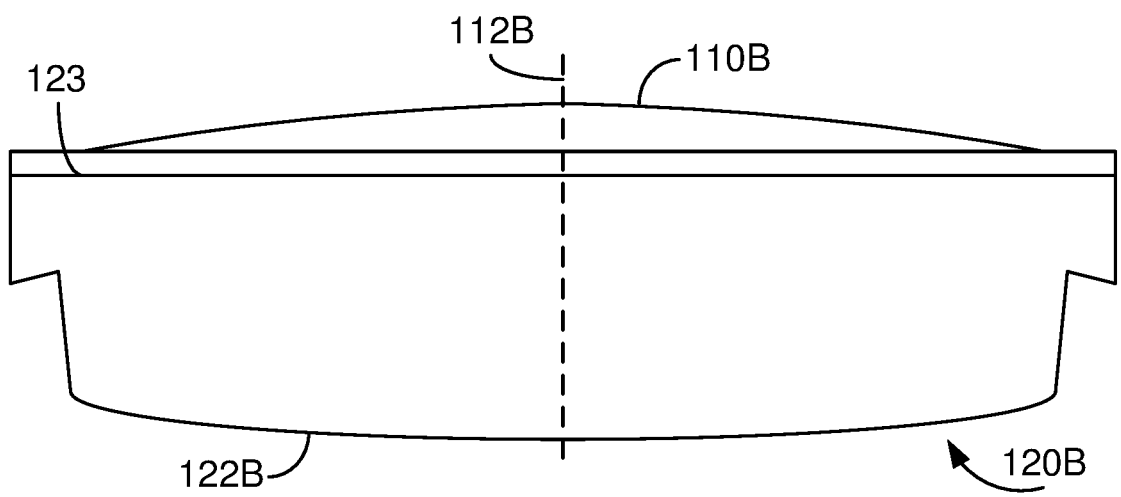
FIG. 3 depicts another exemplary embodiment of an ophthalmic device having multiple Young's moduli.

FIG. 3 depicts a side view of a portion of another exemplary embodiment of an ophthalmic device 100B having multiple Young's moduli and that may be used as or in an IOL. For simplicity, the ophthalmic device 100B is also referred to as an IOL 100 B. For clarity, FIG. 3 is not to scale. The IOL 100B is analogous to the IOLs 100 and/or 100A. Consequently, analogous components have similar labels. The IOL 100B thus includes haptic 120B and optic 110B that are analogous to the haptic 120/120A and optic 110/110A, respectively. The haptic 110B includes frame 122B and arms (not shown) that are analogous to the frame 122/122A and arms 124/124A, respectively. The optic 110B has an optic axis 112B. Although not shown, the anterior and/or posterior surface of the optic 110B may have other features including but not limited to a base curvature and diffraction grating(s). The optic 110B may be fabricated using one or more of a variety of optical materials, as discussed above. The optic 110B may be relatively soft and flexible.

The haptic 120B includes a frame 122B and arms. Although particular shapes are shown for the frame 122B, one of ordinary skill in the art will recognize that the shape of the frame 122B may differ in other embodiments. The frame 122B couples the haptic 120B with the optic 110B. The arms retain the IOL 100A in position in the patient's eye.

The haptic 120B has one or more Young's modulus in the range described above for the haptics 120 and 120A. In addition to supporting and retaining the optic 110B in place, the haptic 120B may also be configured for other purposes.

For example, the haptic 120B may have one or more sharp edges 123. Such edges may address posterior capsular opacification (PCO) by preventing or reducing the growth and/or migration of cells. Such a sharp edge 123 is made possible through the use of higher Young's modulus material(s) in the haptic 120B.

The IOL 100 may share the benefits of the IOL(s) 100 and/or 100A. Use of the higher Young's modulus material(s) in a flexible haptic 120B may allow for the use of a smaller incision during implantation. This less invasive surgery may reduce complications and improve the patient's recovery. The stiffness of various sections of the haptic 120B may also be tailored to withstand higher stresses. Thus, the performance of the haptic 120B both during implantation and throughout its lifetime may be improved. Use of the higher Young's modulus material(s) may also allow the haptic 120B to include the edge 123. Thus, issues such as PCO may be mitigated. Thus, performance of the IOL 100B may be further improved.

Figure 4A:
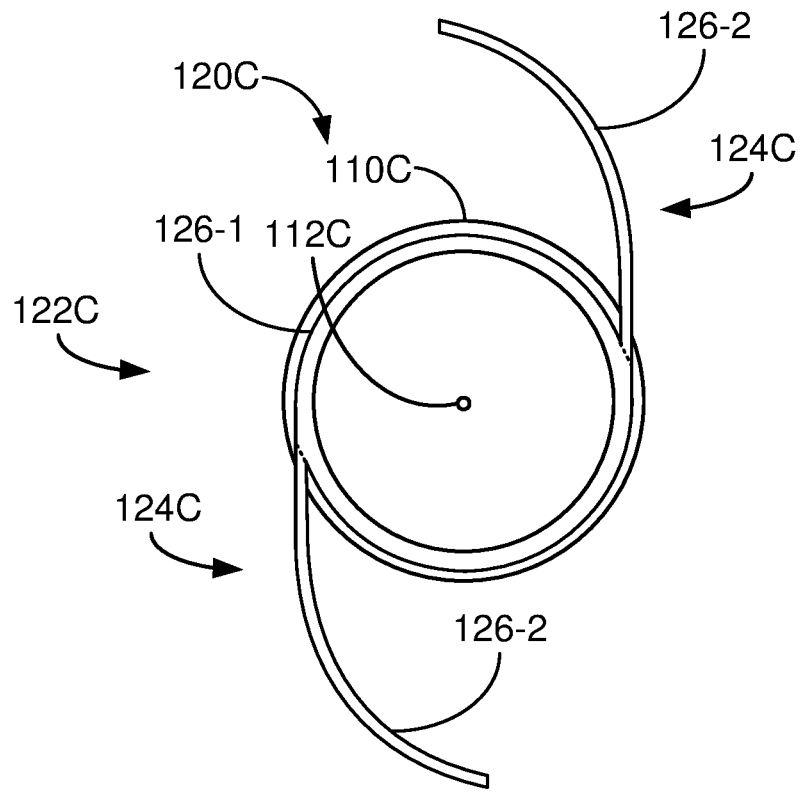
FIGS. 4A and 4B depict various views of an exemplary embodiment of an ophthalmic device having multiple Young's moduli.
Figure 4B:
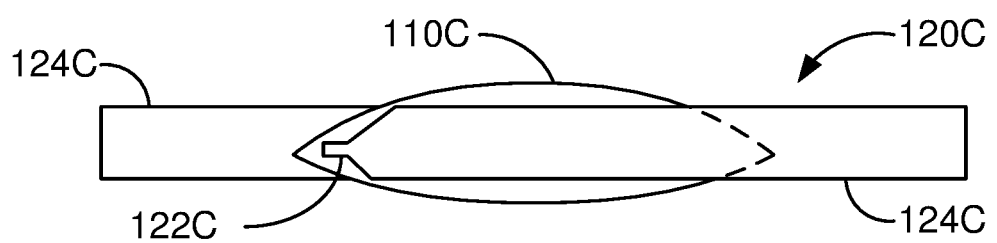

FIGS. 4A-4B depict various views of another exemplary embodiment of an ophthalmic device 100C having multiple Young's moduli. For simplicity, the ophthalmic device 100C is referred to hereinafter as IOL 100C. FIGS. 4A-4B depict plan and side views of portions of the IOL 100C. For clarity, FIGS. 4A-4B are not to scale. For simplicity, the optic axis is not shown. The IOL 100C is analogous to the IOL 100, 100A and/or 100B. Consequently, analogous components have similar labels. The IOL 100C thus includes haptic 120C and optic 110C that are analogous to the haptic 120/120A/120B and optic 110/110A/110B, respectively. The haptic 110C includes frame 122C and arms 124C that are analogous to the frame 122/122A/122B and arms 124/124A, respectively. The optic 110C has an optic axis 112C. Although not shown, the anterior and/or posterior surface of the optic 110C may have other features including but not limited to a base curvature and diffraction grating(s). The optic 110C may be fabricated using one or more of a variety of optical materials, as discussed above. The optic 110C may be relatively soft and flexible.

The haptic 120C includes a frame 122C and arms 124C. Although particular shapes are shown for the frame 122C and arms 124C, one of ordinary skill in the art will recognize that the shape of the frame 122C and arms 124C may differ in other embodiments. The arms 124A retain the IOL 100A in position in the patient's eye.

The haptic 120C explicitly includes multiple materials having different Young's moduli. Thus, the haptic 120C is shown as having regions 126-1 and 126-2 having two different Young's moduli. In other embodiments, the haptic 120C may be formed of a single material or include more material(s) having additional Young's moduli. In some embodiments, all regions 126-1 and 126-2 of the haptic 120C have a higher Young's modulus than any portion of the optic 110C. In some embodiments, each portion 126-1 and 126-2 also has a Young's modulus that is less than 1.8 GPa. In alternate embodiments, only some of the regions 126-1 and 126-2 have a Young's modulus in this range. The differing Young's moduli may be selected to reinforce locations that experience higher stresses, or may be tailored for other reasons. In some embodiments, the cross-section of the haptic 120C may differ at different portions of the haptic. Thus, the combination of the cross-sectional area and the Young's modulus of portions of the haptic 120C may be tailored to provide the desired stiffness and size. In some embodiments, the haptic 120C may be machined.

The frame 122C couples the haptic 120C with the optic 110C. In the embodiment shown, the frame 122C is also has a wider but thinner cross section than the arms 124C. However, other shapes for the frame 122C are possible. In addition, the frame 122C is within the optic 110C. Stated differently, the optic 110C is overmolded around the frame 122C. For example, the frame 122C may be placed in a mold having a diameter larger than the frame 122C. The optical material(s) for the optic 110C are introduced into the mold and solidified, for example via curing. Thus, the frame 122C need not be bonded to the exterior of the optic 110C.

The IOL 100C may share the benefits of the IOLs 100, 100A and/or 100B. Because higher Young's modulus materials are used for the haptic 120C than for the optic 110C, the volume of the haptic 120C may be reduced. Because the Young's modulus materials of the haptic 120C are sufficiently low, the haptic 120C is still flexible. Thus, the IOL 100C may be deformed and implanted through a smaller incision. This less invasive surgery may reduce complications and improve the patient's recovery. Use of the frame 122C may allow for softer material(s) to be used in and larger deformations of the optic 110C. The optic volume may also be reduced. The size of the incision may again be reduced. If multiple materials are used in the haptic 120C, the stiffness of various sections of the haptic 120C may be tailored to withstand higher stresses or strains. Thus, the performance of the haptic 120C both during implantation and throughout its lifetime may be improved. Consequently, performance of the IOL 100C may be further improved.

Figure 5A:
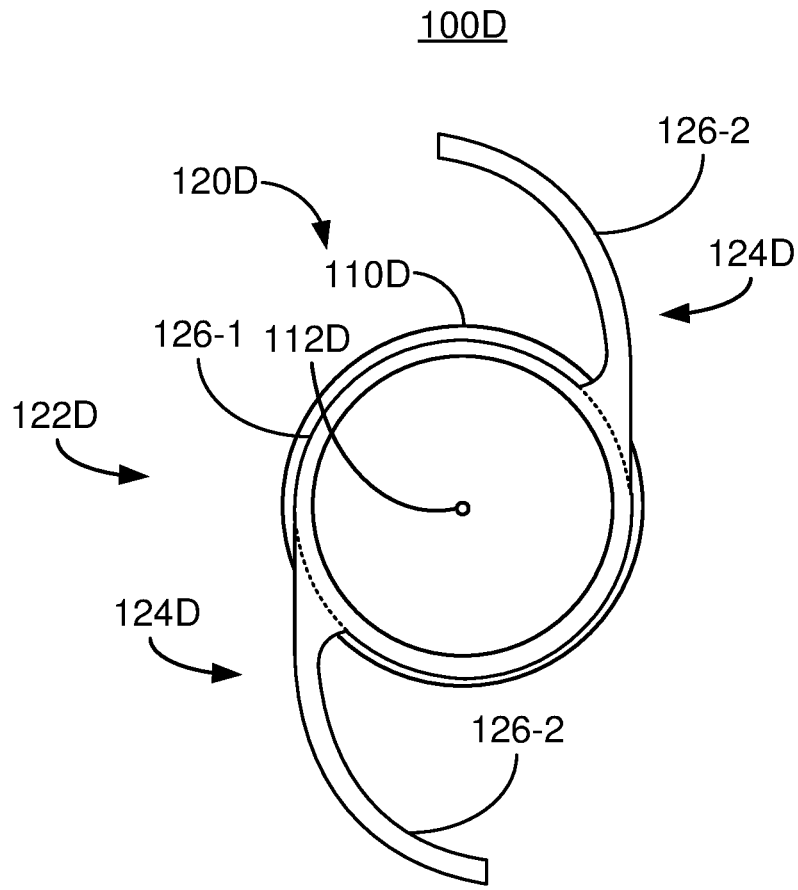
FIGS. 5A and 5B depict various views of an exemplary embodiment of an ophthalmic device having multiple Young's moduli.
Figure 5B:
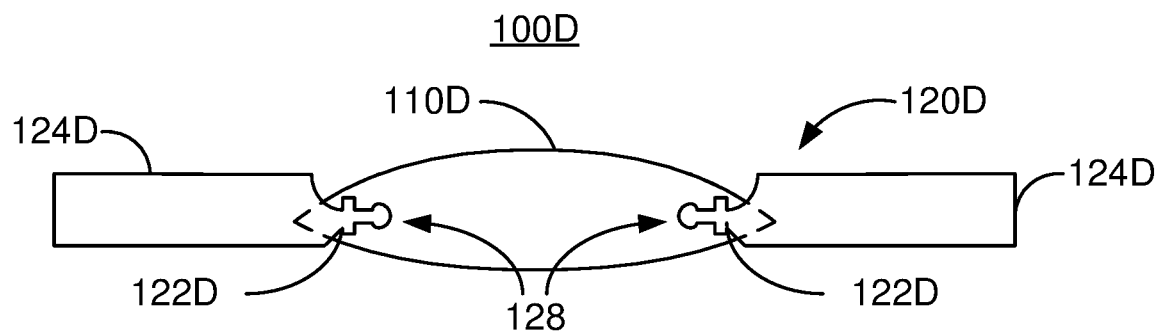

FIGS. 5A-5B depict various views of another exemplary embodiment of an ophthalmic device 100D having multiple Young's moduli. For simplicity, the ophthalmic device 100D is referred to hereinafter as IOL 100D. FIGS. 5A-5B depict plan and side views of portions of the IOL 100D. For clarity, FIGS. 5A-5B are not to scale. For simplicity, the optic axis is not shown. The IOL 100D is analogous to the IOL 100, 100A, 100b and/or 100C. Consequently, analogous components have similar labels. The IOL 100D thus includes haptic 120D and optic 110D that are analogous to the haptic 120/120A/120B/120C and optic 110/110A/110B/110C, respectively. The haptic 110D includes frame 122D and arms 124D that are analogous to the frame 122/122A/122B/ 122C and arms 124/124A/124C, respectively. The optic 110D has an optic axis 112D. Although not shown, the anterior and/or posterior surface of the optic 110D may have other features including but not limited to a base curvature and diffraction grating(s). The optic 110D may be fabricated using one or more of a variety of optical materials, as discussed above. The optic 110D may be relatively soft and flexible.

The haptic 120D includes a frame 122D and arms 124D. Although particular shapes are shown for the frame 122D and arms 124D, one of ordinary skill in the art will recognize that the shape of the frame 122D and arms 124D may differ in other embodiments. The arms 124D retain the IOL 100D in position in the patient's eye.

The haptic 120D may include multiple materials having different Young's moduli. Thus, the haptic 120D is shown as having regions 126-1 and 126-2 having two different Young's moduli. In other embodiments, the haptic 120D may be formed of a single material or include more material(s) having additional Young's moduli. In some embodiments, all regions 126-1 and 126-2 of the haptic 120D have a higher Young's modulus than any portion of the optic 110D. In some embodiments, each portion 126-1 and 126-2 also has a Young's modulus that is less than 1.8 GPa. In alternate embodiments, only some of the regions 126-1 and 126-2 have a Young's modulus in this range. The differing Young's moduli may be selected to reinforce locations that experience higher stresses, or may be tailored for other reasons. In some embodiments, the cross-section of the haptic 120D may differ at different portions of the haptic. Thus, the combination of the cross-sectional area and the Young's modulus of portions of the haptic 120D may be tailored to provide the desired stiffness and size. In some embodiments, the haptic 120D may be machined.

The frame 122D couples the haptic 120D with the optic 110D. In the embodiment shown, the frame 122D is also has a wider but thinner cross section than the arms 124D. Other shapes are possible for the frame 122. In addition, the optic 110D is overmolded around the frame 122D. For example, the molding may be performed in a manner analogous to that discussed above for the IOL 100C. Thus, the frame 122D need not be bonded to the exterior of the optic 110D. In addition, the frame 122D includes features 128 to improve the bonding of the optic 110D material with the frame 122D.

The IOL 100D may share the benefits of the IOLs 100, 100A, 100B and/or 100C. Because higher Young's modulus materials are used for the haptic 120D than for the optic 110D, the volume of the haptic 120D may be reduced. Because the Young's modulus materials of the haptic 120D are sufficiently low, the haptic 120S is still flexible. Thus, the IOL 100D may be deformed and implanted through a smaller incision. This less invasive surgery may reduce complications and improve the patient's recovery. Use of the frame 122D may allow for softer material(s) to be used in and larger deformations of the optic 110D. The optic volume may also be reduced. The size of the incision may again be reduced. If multiple materials are used in the haptic 120D, the stiffness of various sections of the haptic 120D may be tailored to withstand higher stresses or strains. Thus, the performance of the haptic 120D both during implantation and throughout its lifetime may be improved. Consequently, performance of the IOL 100D may be further improved.

Various features of the IOLs 100, 100A, 100B, 100C and 100D have been described herein. One of ordinary skill in the art will recognize that one or more of these features may be combined in manners not explicitly disclosed herein and that are not inconsistent with the method and apparatus described.

Figure 6:
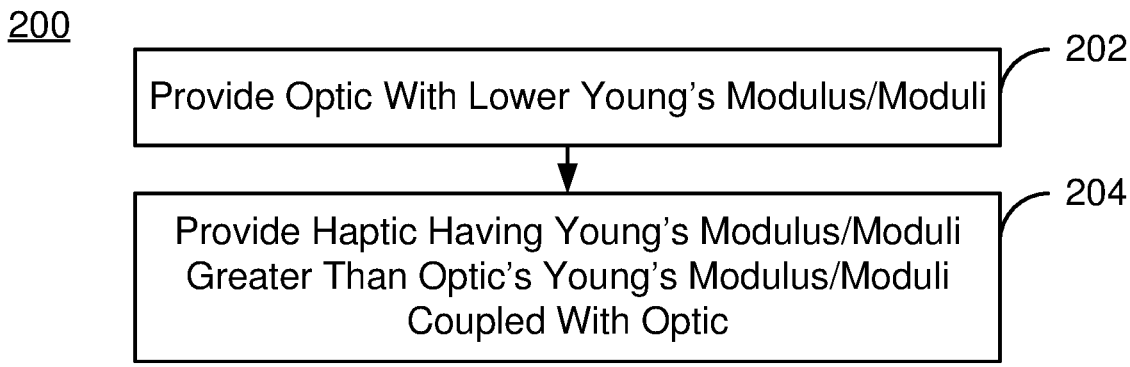
FIG. 6 is a flow chart depicting an exemplary embodiment of a method for providing an ophthalmic device having multiple Young's moduli.

FIG. 6 is a flow chart depicting an exemplary embodiment of a method 200 for providing an IOL having multiple Young's moduli. For simplicity, some steps may be omitted, interleaved, and/or combined. The method 200 is also described in the context of the ophthalmic device 100. However, the method 200 may be used with one or more of IOLs 100A, 100B, 100C, 100D and/or an analogous ophthalmic device.

The optic 110 is provided, via step 202. Step 202 includes providing the optic 110 of a flexible optic material.

The haptic 120 is provided, via step 304. Step 204 may include forming the haptic 120 of one or more materials having a Young's modulus greater than that of the optic 110 and less than 1.8 GPa. Thus, step 204 may include forming the haptic 120 of a single material or of multiple materials that may have different Young's moduli. Step 204 may also include determining the desired locations of higher Young's modulus material(s), for example to support portions the haptic 120 that may be subject to higher stresses and/or strains. Also in step 204 other structures, such as sharp edges, may be formed on the haptic 120. Step 204 may also include attaching the haptic 120 to the optic 110. For example, step 204 may include bonding the structures 110 and 120 or overmolding the optic 110.

Using the method 200, the IOL 100. 100A, 100B, 100C, 100D and/or an analogous ophthalmic device may be provided. Thus, the benefits of one or more of the IOLs 100, 100A, 100B, 100C and/or 100D may be attained.

Figure 7:
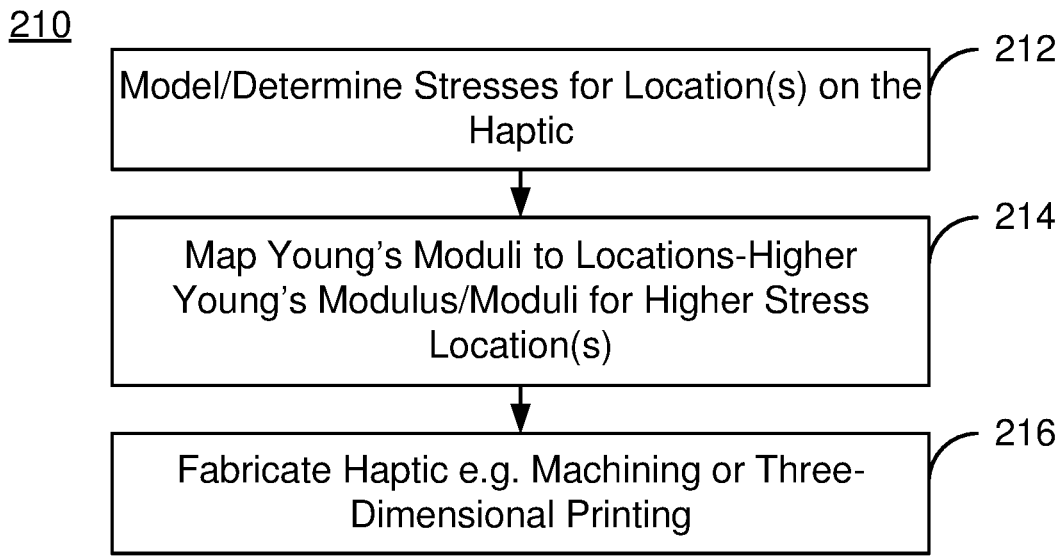
FIG. 7 is a flow chart depicting an exemplary embodiment of a method for providing an ophthalmic device having multiple Young's moduli.

FIG. 7 is a flow chart depicting an exemplary embodiment of a method 210 for providing an IOL having multiple Young's moduli. More specifically, the method 210 is used to form the haptic. For simplicity, some steps may be omitted, interleaved, and/or combined. The method 210 is also described in the context of the ophthalmic device 100A. However, the method 210 may be used with one or more of IOLs 100, 100B, 100C, 100D and/or an analogous ophthalmic device. The method 210 may be viewed as carrying out some or all of the step(s) 202 and/or 204.

The stresses to which the haptic 120A may be subject and the locations of the stresses are determined, via step 212. Step 212 may include modeling the stresses placed on the haptic 120A. For example stresses due to deformation during implantation or use may be modeled.

The desired Young's moduli are mapped to locations on the haptic based on the stresses, via step 214. For example, higher Young's moduli may be mapped to locations that experience higher stresses in step 214. The desired material(s) corresponding to these Young's moduli are also determined in step 214.

The haptic 120A is then fabricated to have the Young's moduli at the appropriate locations, via step 216. Step 216 may include machining the haptic 120A from one or more materials. Portions of the haptic 120A may be three-dimensional printed, molded or otherwise fabricated. If portions having different Young's moduli are formed separately, step 216 also includes integrating the parts of the haptic 120A and affixing them together. Alternatively, one or more of the portions may be formed together. This may occur if the haptic 120A is three-dimensional printed or molded. The haptic 120A may then be coupled with the optic 110A. For example, the haptic 120A may be embedded in the optic 110A via overmolding or may be bonded to the optic 110A. This coupling step may be performed as part of step 202 and/or 204.

Using the method 210, the IOL 100. 100A, 100B, 100C, 100D and/or an analogous ophthalmic device may be provided. Thus, the benefits of one or more of the IOLs 100, 100A, 100B, 100C and/or 100D may be attained.

Figure 8:
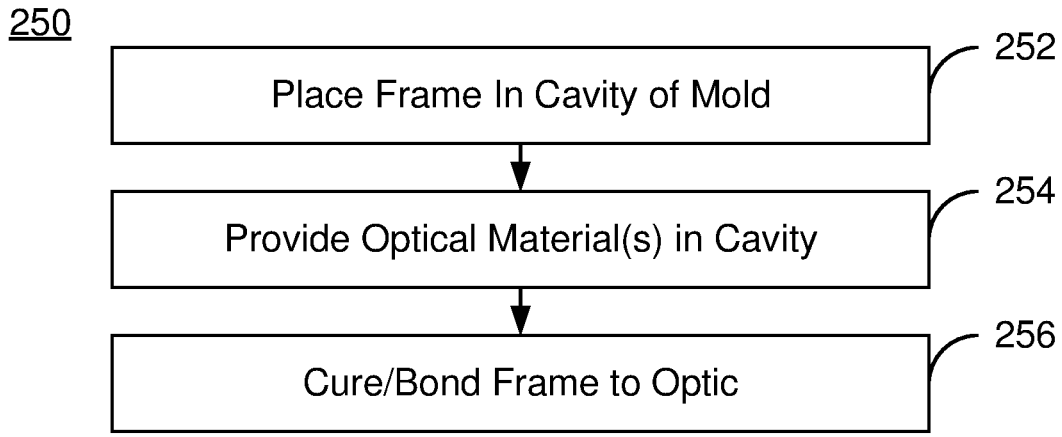
FIG. 8 is a flow chart depicting an exemplary embodiment of a method for providing an ophthalmic device having multiple Young's moduli.

FIG. 8 is a flow chart depicting an exemplary embodiment of a method 250 for providing a portion of an IOL having multiple Young's moduli. More specifically, the method 250 may be used to foam the optic. For simplicity, some steps may be omitted, interleaved, and/or combined. The method 250 is also described in the context of the ophthalmic device 100D. However, the method 210 may be used with one or more of IOLs 100, 100A, 100B, 100C and/or an analogous ophthalmic device. The method 250 may be viewed as carrying out some or all of the step(s) 202 and/or 204.

The frame 122D of the haptic 120D is placed in a cavity of a mold, via step 252. The cavity of the mold has the desired size and shape of the optic 110D. In some embodiments, the cavity is larger than the frame 122D. Thus, the frame 122D will be embedded in the optic 110D.

The optical material(s) for the optic 110D are provided, via step 254. Thus, the optic material(s) are introduced into the cavity. The optic material(s) also cover the frame 110D. In some embodiments, the optical materials are introduced as a liquid so that the cavity is filled.

The optical material(s) are then cured or otherwise bonded to the frame 122B, via step 256. The haptic 120A may thus be coupled with the optic 110A via overmolding or bonding.

Using the method 250, the IOL 100. 100A, 100B, 100C, 100D and/or an analogous ophthalmic device may be provided. Thus, the benefits of one or more of the IOLs 100, 100A, 100B, 100C and/or 100D may be attained.

A method and system for providing an IOL including multiple Young's moduli have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

I claim:

1. An ophthalmic device, comprising:
an optic including at least one optical material having a first Young's modulus; and
a haptic coupled with the optic and including at least a second Young's modulus greater than the first Young's modulus and less than 1.8 GPa such that the haptic is flexible and stiffer than the optic, wherein the haptic includes a frame coupled with the optic and a plurality of arms coupled with the frame; and
wherein the haptic has a higher Young's modulus at regions where the arms meet the frame than at other regions of the haptic.

2. The ophthalmic device of claim 1, wherein inner portions of the frame of the haptic that are affixed to the optic have a lower Young's modulus than outer edges of the frame of the haptic.

3. The ophthalmic device of claim 2, wherein at least a portion of the frame is embedded in a portion of the optic.

4. The ophthalmic device of claim 2, wherein of the frame is bonded to the optic.

5. The ophthalmic device of claim 2, wherein the frame has a sharp edge.

6. The ophthalmic device of claim 1, wherein the haptic is subject to a plurality of characteristic stresses at a plurality of locations and wherein the haptic has a plurality of Young's moduli based on the plurality of locations and the plurality of characteristic stresses.

7. The ophthalmic device of claim 1, wherein tips of the arms of the haptic have a different Young's modulus than other portions of the arms and the frame of the haptic.

8. The ophthalmic device of claim 1, wherein tips of the arms of the haptic have a different Young's modulus than other portions of the arms and the frame of the haptic.

9. An ophthalmic device comprising:
an optic including at least one optical material having a first Young's modulus; and
a haptic coupled with the optic and including a frame and a plurality of arms, the haptic having a plurality of Young's moduli greater than the first Young's modulus and less than 1.8 GPa such that the haptic is flexible and stiffer than the optic, the haptic being subject to a plurality of characteristic stresses at a plurality of locations, and the plurality of Young's moduli at the plurality of locations are based on the plurality of characteristic stresses, wherein the haptic has a higher Young's modulus at regions where the arms meet the frame than at other regions of the haptic, and inner portions of the frame of the haptic that are affixed to the optic have a lower Young's modulus than outer edges of the frame of the haptic.

* * * * *